United States Patent [19]

Kohn et al.

[11] Patent Number: 5,066,482

[45] Date of Patent: Nov. 19, 1991

[54] COMPOSITIONS AND METHOD FOR CONTROLLING COCKROACHES

[75] Inventors: Gustave K. Kohn, Los Altos, Calif.; Robin R. Rudolph, Grand Prairie, Tex.; Gerardus B. Staal, Palo Alto; David L. Grant, Menlo Park, both of Calif.; Robert C. Pearce, Arlington; Barbara A. Herbst, Flower Mound, both of Tex.

[73] Assignee: Sandoz Ltd., Switzerland

[21] Appl. No.: 518,274

[22] Filed: May 4, 1990

Related U.S. Application Data

[63] Continuation of Ser. No. 300,152, Jan. 19, 1989, abandoned, which is a continuation of Ser. No. 167,079, Mar. 11, 1988, abandoned, which is a continuation-in-part of Ser. No. 928,071, Nov. 6, 1986, abandoned, which is a continuation-in-part of Ser. No. 733,444, Jul. 29, 1985, abandoned.

[51] Int. Cl.⁵ .................... A01N 37/06; A61L 9/04
[52] U.S. Cl. .................................... 424/45; 514/549
[58] Field of Search ........................ 424/45; 514/549

[56] References Cited

U.S. PATENT DOCUMENTS 4,021,461  5/1977  Hewrick .................... 260/410.9 N
4,344,959  8/1982  Novak et al. ........................ 514/549

FOREIGN PATENT DOCUMENTS 1414607  11/1975  United Kingdom ................ 514/549

OTHER PUBLICATIONS

Henrick, C. A. et al, *J. Agr. Food Chem* (1973), vol. 21, No. 3, pp. 354–359.
Riddiford, L. M. et al., *J. of Econ. Entn.* (1975) vol. 68, No. 1, pp. 46–48.
Henrick, C. A., et al, *J. Agric Food Chem.* (1975) vol. 23, No. 3, pp. 396–400.
Henrick, C. A. et al, *J. Agric. Food Chem.* (1976) vol. 24, No. 2, pp. 207–218.
Henrick, C. A. et al, *J. Agric. Food Chem.* (1978), vol. 26, No. 3, pp. 542–550.
Henrick, C. A., "Insecticides Made of Action", Chap. 11, Copyright 1982 by Academic Press Inc., pp. 315, 333–355, 382–386.
Steal, G. B. et al, "Cockroach Control with Juvenoids", Proceedings of the Conf. on New Concepts in Pesticide Chemistry (Snowbird, Utah, Jun. 1984).
Kovalick & Koeppe, Molecular & Cellular Endocrinology 31 (1983) 271–286.

*Primary Examiner*—Allen J. Robinson
*Attorney, Agent, or Firm*—Allen E. Norris

[57] ABSTRACT

The invention relates to novel compositions and methods for controlling cockroach populations using the (S)-(+) enantiomer of hydroprene.

10 Claims, No Drawings

COMPOSITIONS AND METHOD FOR CONTROLLING COCKROACHES

This application is a continuation of Ser. No. 300,152, filed on Jan. 19, 1989, now abandoned, which is a continuation of Ser. No. 167,079, filed Mar. 11, 1988, now abandoned, which is a continuation-in-part of Ser. No. 928,071, filed Nov. 6, 1986, now abandoned, which is a continuation-in-part of Ser. No. 733,444, filed July 29, 1985, now abandoned.

TECHNICAL FIELD

This invention is in the field of pest control. More specifically, it relates to novel compositions and methods for controlling cockroach populations using the (S)-(+) enantiomer of hydroprene.

BACKGROUND ART

Hydroprene is ethyl (2E,4E)-3,7,11-trimethyl-2,4-dodecadienoate and is described and claimed in U.S. Pat. No. 4,021,461. It is known to have juvenile hormone activity on insects, *J Agric Food Chem* (1973) 21:354–359; *J Agric Food Chem* (1976) 24:207–218 The juvenile hormone activity of hydroprene (racemic mixture) on *Blatella germanica* (German cockroach) is reported in *J Econ Entom* (1975) 68:46–48.

There is an asymmetric carbon atom at C-7 in hydroprene and, accordingly, there are R and S enantiomers of the compound. *J Agric Food Chem* (1978) 26:542–550 reports comparative juvenile hormone activity tests on (S)-(+) hydroprene, (R)-(−) hydroprene and the racemic mixture on *Aedes aegypti, Galleria mellonella, Tenebrio molitor, Musca domestica,* and *Heliothis virescents.* These tests showed that the (S)-(+) enantiomer showed approximately twice the activity of the racemic mixture on these insect species. This 2:1 activity ratio is typical of racemic mixtures in which one of the optical isomers is the predominant biologically active species.

DISCLOSURE OF THE INVENTION

It has now surprisingly been found that (S)-(+) hydroprene exhibits unexpectedly superior juvenile hormone activity on cockroaches relative to racemic hydroprene. This discovery was surprising in view of the above mentioned prior report that (S)-(+) hydroprene showed only the expected 2:1 activity ratio relative to the racemic mixture on a number of insect species.

Accordingly, one aspect of the invention is a method of cockroach population control comprising administering a cockroach reproduction inhibiting amount of (S)-(+) hydroprene to the locus infested by said population.

The term "(S)-(+) hydroprene" as used herein is intended to relate to hydroprene comprising substantially from more than 50% to 100% by weight of the (S)-(+) enantiomer. Preferably the hydroprene used in the invention is composed predominantly of (S)-(+) hydroprene, i.e. comprises from more than 75% to 100% by weight of (S)-(+) hydroprene. More preferably, the hydroprene contains less than 10%, particularly less than 5% by weight of the (R) enantiomer and is most preferably substantially free of the (R) enantiomer (i.e. contains less than 2% by weight of the (R) enantiomer).

Another aspect of the invention is a pest controlling composition comprising:
a) (S)-(+) hydroprene
b) a diluent
and c) where the diluent is a solvent, at least one adjuvant selected from a propellant, a surfactant and a thickener (hereinafter composition of the invention).

The term "diluent" as used herein means any liquid or solid agriculturally acceptable material which may be added to the active ingredient to bring it in an easier or improved applicable form. It includes carriers and solvents and can for example be calcium carbonate, talc, kaolin, clay, silica, diatomaceous earth, resins (such as polyvinyl chloride, polyester urethane, ethylene vinyl acetate, polypropylene), polyethylene, xylene, a petroleum solvent (including ligroin, benzene, naphtha, a hydrocarbon such as pentane, hexane, octane), an alkanol such as isopropanol, a chlorinated hydrocarbon (e.g. $CH_2Cl_2$, $CCl_3CH_3$), glycol monoalkylether, water and the like.

The term "propellant" relates to an agriculturally acceptable liquified gas which is self pressurised in a container having a valve and comprising a pest controlling composition, which gas forces the contents from the container when the valve is activated.

The term "surfactant" relates to an agriculturally acceptable material which imparts emulsifiability, spreading, wetting, dispersibility or other surface-modifying properties to the pest controlling composition of the invention.

The term "thickener" relates to a material which increases the viscosity of a liquid.

MODES FOR CARRYING OUT THE INVENTION (S)-(+) hydroprene may be obtained in a manner known per se by resolving hydroprene into the (S) and (R) enantiomers or by synthesizing (S)-(+) hydroprene from a resolved starting material. *J. Agric. Food Chem.* (1978) 26:542–550 describes embodiments of this latter technique. The procedures described in U.S. Pat. No. 4,021,461 using a resolved starting material may also be employed.

(S)-(+) hydroprene exhibits a unique combination of properties vis-a-vis other juvenoids that makes it remarkably effective as a cockroach population control agent.

It is persistent in the environments that cockroaches inhabit. It is sufficiently volatile to translocate from one surface to another and thus penetrate into cockroach harborages, redistribute therein, and remain accessible to resident cockroach populations. Further, (S)-(+) hydroprene is effective in inducing sterility in cockroaches as well as having other juvenoid activities. This property is essential to effective cockroach eradication. Finally, (S)-(+) hydroprene has a high level of activity. Its superior activity relative to racemic hydroprene means that it is much more economical to use and provides less contamination of food and the human habitat than the racemic mixture.

In this regard, substantially pure (S)-(+) hydroprene has been found to provide German cockroach reproduction control in the laboratory at distribution levels as low as a few tenths of a microgram per square meter. Higher distribution levels may be required to control populations of other cockroach species such as the American cockroach (*Periplaneta americana*) and the oriental cockroach (*Blatta orientalis*). Also, in actual use in the field higher distribution levels than were used in the laboratory are used. Thus, depending on the nature of the surfaces in the habitat, the cockroach species, the mode of application, etc., the distribution level of (S)-(+) hydroprene in actual use will conveniently be in the range of 0.3 mg/m² to 40 mg/m², more preferably of 3 mg/m² to 30 mg/m².

(S)-(+) hdyroprene is typically applied in composition form suitable for use in cockroach control. Examples of compositions suitable for such use comprise aerosols (in aerosol dispensers or foggers), cockroach baits, cockroach dusts, emulsifiable concentrates, ready-to-use sprays, ultra low volume sprays, aroma disks, cockroach strips, floor waxes and polishes and the like; such compositions may be obtained in conventional manner. The composition of the invention is conveniently applied to cockroach habitats, which habitats include but are not limited to human lodgings, sites where food is stored or prepared and industrial facilities. The vapors of (S)-(+) hydroprene may initially penetrate into the cockroach habitat, or because of the volatility of the material, translocate from initial or intermediate sites of deposit to the cockroach habitat.

For use of (S)-(+) hydroprene in aerosol form, the active ingredient is conveniently formulated with an innocuous, volatile solvent and a propellant.

Examples of suitable volatile solvents are chlorinated alkanes such as methylene chloride or 1,1,1-trichloroethane.

Examples of suitable propellants are low-boiling alkanes such as propane or butane or fluorinated hydrocarbons.

For use of (S)-(+) hydroprene in spray form, e.g. as emulsifiable concentrate or ready-to-use spray, the active ingredient will conveniently be formulated with an emulsifying agent and a solvent.

Examples of suitable emulsifiers are sorbitol, fatty acid esters, polyethoxylated fatty acid esters of alcohols or phenols, calcium dodecyl benzoate and the like.

Examples of suitable solvents are aromatic hydrocarbons such as xylene.

Solid compositions such as dusts or powders comprise (S)-(+) hydroprene and a solid carrier.

Examples of suitable solid carriers are calcium carbonate, diatomaceous earth, clay, silica and the like.

(S)-(+) hydroprene may also be applied in solid composition form by evaporation from a solid carrier, e.g. in the form of floor waxes and polishes, aroma disks and strips, particularly the latter.

Solid compositions such as aroma disks and strips will comprise (S)-(+) hydroprene, a polymer and, preferably a plasticizer.

Examples of suitable polymers (resins) are polyvinyl chloride, polyethylene, polyurethane, polypropylene, acrylics, nylon, in particular polyvinyl chloride.

For use of (S)-(+) hydroprene in bait form, the active ingredient will conveniently be formulated with a foodstuff.

Suitable foodstuffs for use in such baits are corn meal, dog food, corn syrup and the like.

(S)-(+) hydroprene may also be used in microencapsulated form. Such microcapsules are conveniently of the gelatin or nylon type; compositions comprising microcapsules contain conveniently a thickener such as xanthan gum.

The (S)-(+) hydroprene formulations of the invention may contain conventional additives such as U.V. stabilizers, heat stabilizers, antioxidants, pigments, etc. They may also contain conventional insecticides such as organophosphates and pyrethroids to provide an initial knockdown of a portion of the cockroach population or other insects at the application site. Conventional contact insecticides that provide an initial kill of adult cockroaches can be included for buyer acceptance reasons rather than their impact on controlling the resident cockroach population. Such formulations are prepared in a manner known per se.

Suitable compositions of the invention comprise conveniently from 0.01 to 80% by weight of (S)-(+) hydroprene. Conveniently aerosols will comprise from 0.01 to 10% by weight, emulsifiable concentrates and ultra low volume sprays from 0.3 to 80% by weight, ready-to-use sprays from 0.5 to 10% by weight and cockroach baits or strips from 0.5 to 15% by weight of (S)-(+) hydroprene.

The invention is further illustrated by the following examples. These examples are not intended to limit the invention in any manner. Parts are by weight.

FORMULATION EXAMPLES

Example A

Aerosol (S)-(+) hydroprene was formulated into a 3 oz total release aerosol fogger at 0.02% active ingredient (AI) and 0.06% AI. For comparison, hydroprene (racemic mixture) and standard commercial IGR (fenoxycarb) were formulated similarly. Details of the formulations are given in Table 1 below.

TABLE 1

| | Formula (wt %) | | | | | |
|---|---|---|---|---|---|---|
| Ingredient | A S-hydroprene 0.02% AI | B S-hydroprene 0.06% AI | C hydroprene 0.02% AI | D hydroprene 0.06% AI | E Standard Commercial IGR 0.02% AI | F Standard Commercial IGR 0.06% AI |
| S-hydroprene (94%) | 0.021 | 0.064 | — | — | — | — |
| hydroprene (R-S, 92.6%) | — | — | 0.022 | 0.065 | — | — |
| Standard Commercial IGR (98%) | — | — | — | — | 0.020 | 0.061 |
| Aerothene MM[1] | 17.646 | 16.936 | 17.645 | 16.935 | 17.647 | 16.939 |
| Aerothene TT[2] | 54.333 | 55 | 54.333 | 55 | 54.333 | 55 |
| Propellant A-70[3] | 28 | 28 | 28 | 28 | 28 | 28 |

[1] methylene chloride
[2] 1,1,1-trichloroethane
[3] propane/isobutane to 70 psi

Example B

Emulsifiable concentrate

| | |
|---|---|
| (S)-(+) hydroprene (100%) | 10.0 |
| antioxidant | 0.2 |
| (butylated hydroxytoluene) | |
| emulsifier | 30.8 |
| (polyoxyethylene sorbitol ester) | |
| solvent | 59.0 |
| (aliphatic hydrocarbon) | |

Example C

Ready-to-use spray

| | |
|---|---|
| (S)-(+) hydroprene (100%) | 0.4 |
| water | 91.86 |
| antioxidant | 0.44 |
| (butylated hydroxytoluene) | |
| emulsifier | 2.0 |
| (polyoxyethylene sorbitol ester) | |
| chelating agent (NaEDTA) | 5.0 |
| buffering agent (citric acid) | 0.3 |

Example D

Bait

| | |
|---|---|
| (S)-(+) hydroprene (100%) | 1.0 |
| $CH_2Cl_2$ | 5.0 |
| corn meal | 94.0 |

Example E

Dust

| | |
|---|---|
| (S)-(+) hydroprene (100%) | 10.0 |
| Ethylene glycol | 4.5 |
| Antioxidant | 0.5 |
| (butylated hydroxy toluene) | |
| silica | 85.0 |

Example F

Insect strip

| | |
|---|---|
| (S)-(+) hydroprene (100%) | 0.79 |
| polymer (polyvinyl chloride) | 65.0 |
| plasticizer (dioctyl adipate) | 28.21 |
| plasticizer (dioctyl phthalate) | 3.0 |
| vinyl stabilizer | 3.0 |
| (metallic soap) | |

Example G

| | |
|---|---|
| water | 20.90 |
| acrylic emulsion | 1.92 |
| fluorocarbon surfactant | 0.69 |
| silicone antifoam | 0.02 |
| solvent | 5.64 |
| (diethyl glycol monoethyl ether) | |
| tributyloxyethylphosphate | 1.29 |
| anti-microbial agent | 0.14 |
| acrylic copolymer | 58.42 |
| polymeric emulsion | 10.95 |
| (S)-(+) hydroprene (90%) | 0.03 |

BIOASSAY EXAMPLES

Test 1

Foggers comprising 15 mg and 45 mg of (S)-(+) hydroprene resp., formulated according to Formulation Examples A-A and A-B resp., are discharged in 85 m3 fogger chambers. Foggers containing racemic hydroprene and formulated similarly (Examples A-C and A-D) are also similarly discharged for comparison. At the time of discharge the chamber contained cigarette papers and three different test substrates (treated vinyl tile, glass, and unpainted plywood) placed at distances of 1.8, 2.7 and 3.7 m from the fogger. The mist is allowed to settle for 20 minutes and the papers and substrates are removed. The papers are extracted and the extracts analysed to determine the amount of hydroprene (in ug/cm$^2$ substrate) deposited at the three distances. The depositions of (S)-(+) hydroprene are in the range of 0.005 to 0.053 ug/cm$^2$. The depositions of racemic hydroprene are in the range of 0.011 to 0.036 ug/cm$^2$. The depositions are reported in Table 2 below.

TABLE 2

| Formula (wt %) | Deposition µg AI/cm$^2$ | | |
|---|---|---|---|
| Formula | 1.8 m | 2.7 m | 3.7 m |
| S-hydroprene 0.02% | 0.011 | 0.010 | 0.005 |
| S-hydroprene 0.06% | 0.053 | 0.053 | 0.038 |
| hydroprene 0.02% | 0.012 | 0.011 | 0.011 |
| hydroprene 0.06% | 0.034 | 0.036 | 0.032 |
| Standard Commercial IGR 0.02% | 0.026 | 0.026 | 0.023 |
| Standard Commercial IGR 0.06% | 0.084 | 0.076 | 0.069 |

After removal from the chamber the treated test substrates are placed in a laboratory under ambient conditions. Within one hour of removal, ten to twelve fifth to sixth instar German cockroaches are confined to each of the treated substrate surfaces. Food, water and harborage are supplied.

The containers are examined daily for the first ten days. At the examination times food and water are replenished as needed. All cockroaches molting to the adult stage are removed and destroyed during the first ten days of the test. (Roaches in the last ten days of the last instar before molt are not sensitive to juvenoids.)

After day ten the containers are examined every seven to fourteen days and the following status information recorded.

Total number of surviving cockroaches.
Adult or nymph, status of each cockroach.
Sex of all adult cockroaches.
JH effect on adult cockroaches if any.
Ootheca carried.
Viability of ootheca dropped.
$F_1$ progeny produced.

The final reading is taken at week 12 after the ten-day post-treatment period.

Based on these readings the treatments are scored for overall juvenile hormone (JH) effects.

The overall JH response of (S)-(+) hydroprene was significantly better than the racemic mixture which was used as standard, as shown in Table 3. More importantly, the results of the readings on total $F_1$ nymphs produced and $F_1$ nymphs produced per female cockroach having the opportunity to mate and produce young indicate (as shown in Table 4) that the reproduction control activity of (S)-(+) hydroprene was about 7-fold higher than the racemic mixture and even higher with respect to the standard commercial IGR.

with the racemic mixture and a leading commercial insect growth regulator. In the case of the standard commercial IGR, reproduction occurred even at depositions that provided a 100% overall JH response. Also

TABLE 3

| Treatment | Percent of Adult Roaches Showing JH Characteristics at Indicated Week Past Treatment | | | | | | | | |
|---|---|---|---|---|---|---|---|---|---|
| | 4 | 5 | 6 | 7 | 8 | 9 | 10 | 11 | 12 |
| On Wood | | | | | | | | | |
| S-hydroprene 0.02% | 56% | 52% | 56% | 46% | 43% | — | 46% | — | 46% |
| S-hydroprene 0.06% | 100% | 100% | 97% | 88% | 85% | — | 84% | — | 82% |
| Hydroprene 0.02% | 24% | 27% | 29% | 30% | 44% | — | 29% | — | 29% |
| Hydroprene 0.06% | 73% | 76% | 57% | 53% | 49% | — | 44% | — | 44% |
| Standard Commercial IGR 0.02% | 53% | 45% | 42% | 41% | 33% | — | 44% | — | 47% |
| Standard Commercial IGR 0.06% | 93% | 92% | 88% | 87% | 86% | — | 82% | — | 90% |
| On Glass | | | | | | | | | |
| S-hydroprene 0.02% | 30% | 26% | 26% | 29% | 22% | — | 23% | — | 23% |
| S-hydroprene 0.06% | 82% | 87% | 77% | 74% | 70% | — | 63% | — | 65% |
| Hydroprene 0.02% | 48% | 49% | 48% | 49% | 52% | — | 50% | — | 48% |
| Hydroprene 0.06% | 35% | 40% | 30% | 33% | 32% | — | 27% | — | 27% |
| Standard Commercial IGR 0.02% | 100% | 100% | 100% | 100% | 97% | — | 94% | — | 97% |
| Standard Commercial IGR 0.06% | 100% | 100% | 100% | 100% | 100% | — | 100% | — | 100% |
| On Tile | | | | | | | | | |
| S-hydroprene 0.02% | 67% | 69% | 59% | 59% | 56% | — | 58% | — | 60% |
| S-hydroprene 0.06% | 77% | 86% | 92% | 91% | 92% | — | 94% | — | 83% |
| Hydroprene 0.02% | 28% | 45% | 48% | 40% | 45% | — | 46% | — | 44% |
| Hydroprene 0.06% | 82% | 85% | 84% | 68% | 65% | — | 63% | — | 60% |
| Standard Commercial IGR 0.02% | 29% | 28% | 33% | 25% | 33% | — | 33% | — | 33% |
| Standard Commercial IGR 0.06% | 77% | 73% | 69% | 58% | 67% | — | 66% | — | 65% |
| On all Surfaces | | | | | | | | | |
| S-hydroprene 0.02% | 48% | 48% | 46% | 44% | 40% | — | 38% | — | 43% |
| S-hydroprene 0.06% | 89% | 92% | 90% | 85% | 83% | — | 82% | — | 78% |
| Hydroprene 0.02% | 36% | 42% | 41% | 40% | 44% | — | 42% | — | 41% |
| Hydroprene 0.06% | 63% | 67% | 57% | 51% | 48% | — | 45% | — | 45% |
| Standard Commercial IGR 0.02% | 54% | 53% | 46% | 53% | 52% | — | 53% | — | 55% |
| Standard Commercial IGR 0.06% | 90% | 89% | 88% | 83% | 84% | — | 82% | — | 84% |

TABLE 4

| Treatment | Ootheca Carried | Non-Viable Ootheca | Dead in Molt Attempt | Dead Nymph | Dead JH Adult | Dead N. Adult | $F_1$ Nymphs Produced at indicated Week | | | $F_1$ Nymph/ FR |
|---|---|---|---|---|---|---|---|---|---|---|
| | | | | | | | Week 8 | Week 10 | Week 12 | |
| S-hydroprene | 166 | 56 | 4 | 6 | 2 | — | 0 | 0 | 95 | 0.6 |
| hydroprene | 243 | 44 | 4 | 3 | 7 | 3 | 0 | 450 | 703 | 4.7 |
| Standard Commercial IGR | 167 | 32 | 1 | 8 | 14 | 1 | 0 | 600 | 865 | 8.6 |

Results are for week twelve except as indicated otherwise.
FR — female roach having the opportunity to mate and reproduce.

As shown in Table 5 below, (S) hydroprene depositions completely prevented reproduction whereas with the racemic hydroprene some reproduction occurred even at the highest rate of 0.036 ug/cm². The data of Table 5 show the unexpectedly superior sterilizing ability of (S)-(+) hydroprene as compared to treatment (S) hydroprene performed better on tile and wood surfaces (which are likely to be present in cockroach habitats) than glass. The standard commercial IGR performance was the opposite—looking better on glass than tile and wood.

TABLE 5

| Treatment | | | | Week 12 $F_1$ Progeny Produced per Indicated Surface | | |
|---|---|---|---|---|---|---|
| Compound | % AI | Distance | Deposition Rate | Tile | Glass | Wood |
| S-hydroprene | 0.02% | 3.7 m | 0.005 μg/cm² | 0 | 95* | 0 |
| S-hydroprene | 0.02% | 2.7 m | 0.010 μg/cm² | 0 | 0 | 0 |
| S-hydroprene | 0.02% | 1.8 m | 0.011 μg/cm² | 0 | 0 | 0 |
| S-hydroprene | 0.06% | 3.7 m | 0.038 μg/cm² | 0 | 0 | 0 |
| S-hydroprene | 0.06% | 2.7 m | 0.053 μg/cm² | 0 | 0 | 0 |
| S-hydroprene | 0.06% | 1.8 m | 0.053 μg/cm² | 0 | 0 | 0 |
| Racemic | 0.02% | 3.7 m | 0.011 μg/cm² | 70 | 150 | 30 |

TABLE 5-continued

| Treatment | | | | Week 12 F₁ Progeny Produced per Indicated Surface | | |
|---|---|---|---|---|---|---|
| Compound | % AI | Distance | Deposition Rate | Tile | Glass | Wood |
| Racemic hydroprone | 0.02% | 2.7 m | 0.011 $\mu g/cm^2$ | 95 | 65 | 70 |
| Racemic hydroprone | 0.02% | 1.8 m | 0.012 $\mu g/cm^2$ | 0 | 0 | 140 |
| Racemic hydroprone | 0.06% | 3.7 m | 0.032 $\mu g/cm^2$ | 0 | 30 | 0 |
| Racemic hydroprone | 0.06% | 2.7 m | 0.036 $\mu g/cm^2$ | 0 | 63 | 0 |
| Racemic hydroprone | 0.06% | 1.8 m | 0.034 $\mu g/cm^2$ | 0 | 0 | 25 |
| Standard Commercial IGR 0.02% | | 3.7 m | 0.023 $\mu g/cm^2$ | 0 | 0 | 202 |
| Standard Commercial IGR 0.02% | | 2.7 m | 0.026 $\mu g/cm^2$ | 178 | 0 | 98 |
| Standard Commercial IGR 0.02% | | 1.8 m | 0.026 $\mu g/cm^2$ | 75 | 0 | 140 |
| Standard Commercial IGR 0.06% | | 3.7 m | 0.069 $\mu g/cm^2$ | 1 | 0 | 14 |
| Standard Commercial IGR 0.06% | | 2.7 m | 0.076 $\mu g/cm^2$ | 0 | 0 | 0 |
| Standard Commercial IGR 0.06% | | 1.8 m | 0.084 $\mu g/cm^2$ | 100 | 0 | 57 |

*values averaged over two replicates, one control showed 0. one (S) hydroprene exhibited high F₁ progeny. It is believed that a mislabel of samples caused this anomaly.

Test 2

Serial dilutions of (S)-(+) hydroprene or racemic hydroprene in acetone are applied to glass and plywood by dribbling the solution onto the plates from a syringe. The plates are used as floors for test cages. Each cage is supplied with harborage, water and food and 50 4th instar German cockroaches. The cages are maintained at 27° C., 16 hours light cycle, 50% relative humidity for about two months. Control efficacy is scored based on morphological effects and 100% inhibition of reproduction. In these tests (S)-(+) hydroprene provided 100% control of reproduction at a distribution of 0.1 ug/cm², whereas the lowest distribution giving 100% control with racemic hydroprene was 10 ug/cm² on glass and 1 ug/cm² on plywood. These results indicate that the reproduction control activity of (S)-(+) hydroprene was 100-fold higher than the racemic mixture on glass and 10-fold higher than the racemic on plywood.

What is claimed is:

1. A method of controlling a cockroach population comprising administering to a cockroach population or its infested habitat a cockroach reproduction inhibiting amount of hydroprene comprising at least 90% of its S-(+) enantiomer.

2. A method according to claim 1 wherein the hydroprene comprises at least 98% of its S-(+) enantiomer.

3. A method according to claim 1 wherein the hydroprene is administered in the form of a spray or aerosol.

4. The method of claim 1 wherein the hydroprene is administered by evaporation from a solid carrier.

5. The method of claim 1 wherein the distribution of hydroprene is in the range of 0.3 to 50 mg/m².

6. The method of claim 1 wherein the cockroach population is a population of German cockroaches.

7. A method according to claim 2 wherein the hydroprene is administered in the form of a spray or aerosol.

8. The method of claim 2 wherein the hydroprene is administered by evaporation from a solid carrier.

9. The method of claim 2 wherein the distribution of hydroprene is in the range of 0.3 to 50 mg/m².

10. The method of claim 2 wherein the cockroach population is a population of German cockroaches.

* * * * *